(12) United States Patent
Bi et al.

(10) Patent No.: US 10,605,880 B2
(45) Date of Patent: Mar. 31, 2020

(54) RESPIRATORY PHASE-RESOLVED 3D BODY IMAGING USING ITERATIVE MOTION CORRECTION AND AVERAGE

(71) Applicants: Siemens Healthcare GmbH, Erlangen (DE); Cedars-Sinai Medical Center, Los Angeles, CA (US)

(72) Inventors: Xiaoming Bi, Oak Park, CA (US); Jianing Pang, Chicago, IL (US); Zhaoyang Fan, Hacienda Heights, CA (US); Matthias Fenchel, Erlangen (DE); Gerhard Laub, San Mateo, CA (US); Debiao Li, South Pasadena, CA (US)

(73) Assignees: Siemens Healthcare GmbH, Erlangen (DE); Cedars-Sinai Medical Center, Los Angeles, CA (US)

( * ) Notice: Subject to any disclaimer, the term of this patent is extended or adjusted under 35 U.S.C. 154(b) by 521 days.

(21) Appl. No.: 15/590,203

(22) Filed: May 9, 2017

(65) Prior Publication Data

US 2017/0328970 A1 Nov. 16, 2017

Related U.S. Application Data

(60) Provisional application No. 62/334,108, filed on May 10, 2016.

(51) Int. Cl.
*G01R 33/565* (2006.01)
*G01R 33/561* (2006.01)
(Continued)

(52) U.S. Cl.
CPC ........ *G01R 33/56509* (2013.01); *A61B 5/055* (2013.01); *G01R 33/5619* (2013.01);
(Continued)

(58) Field of Classification Search
CPC .......... G01R 33/56509; G01R 33/5619; G01R 33/5676; G01R 33/4826; G01R 33/54; G01R 33/5608; A61B 5/055
See application file for complete search history.

(56) References Cited

U.S. PATENT DOCUMENTS

| | | | |
|---|---|---|---|
| 2009/0018433 A1* | 1/2009 | Kassai | A61B 5/055 600/413 |
| 2011/0130644 A1* | 6/2011 | Stemmer | A61B 5/055 600/410 |

(Continued)

OTHER PUBLICATIONS

Akino, Yuichi, et al. "Evaluation of potential internal target volume of liver tumors using cine-MRI." Medical physics 41.11 (2014).

(Continued)

*Primary Examiner* — Bo Joseph Peng

(57) ABSTRACT

A method for performing 3D body imaging includes performing a 3D MRI acquisition of a patient to acquire k-space data and dividing the k-space data into k-space data bins. Each bin includes a portion of the k-space data corresponding to a distinct breathing phase. 3D image sets are reconstructed from the bins, with each 3D image set corresponding to a distinct k-space data bin. For each bin other than a selected reference bin, forward and inverse transforms are calculated between the 3D image set corresponding to the bin and the 3D image set corresponding to the reference bin. Then, a motion corrected and averaged image is generated for each bin by (a) aligning the 3D image set from each other bin to the 3D image set corresponding to the bin using the transforms, and (b) averaging the aligned 3D image sets to yield the motion corrected and averaged image.

19 Claims, 11 Drawing Sheets

(51) Int. Cl.
*G01R 33/567* (2006.01)
*A61B 5/055* (2006.01)
*G01R 33/54* (2006.01)
*G01R 33/48* (2006.01)
*G01R 33/56* (2006.01)

(52) U.S. Cl.
CPC ...... *G01R 33/5676* (2013.01); *G01R 33/4826* (2013.01); *G01R 33/54* (2013.01); *G01R 33/5608* (2013.01)

(56) References Cited

U.S. PATENT DOCUMENTS

| | | | | |
|---|---|---|---|---|
| 2011/0152668 | A1* | 6/2011 | Stemmer | G01R 33/5676 600/413 |
| 2012/0271155 | A1* | 10/2012 | Stemmer | A61B 5/055 600/413 |
| 2016/0324500 | A1* | 11/2016 | Fan | G01R 33/5676 |
| 2017/0135599 | A1* | 5/2017 | Brown | A61M 16/202 |

OTHER PUBLICATIONS

Tryggestad, Erik, et al. "Respiration-based sorting of dynamic MRI to derive representative 4D-MRI for radiotherapy planning." Medical physics 40.5 (2013).

Von Siebenthal, M., et al. "4D MR imaging of respiratory organ motion and its variability." Physics in medicine and biology 52.6 (2007): 1547.

Buerger, Christian, Claudia Prieto, and Tobias Schaeffter. "Highly efficient 3D motion-compensated abdomen MRI from undersampled golden-RPE acquisitions." Magnetic Resonance Materials in Physics, Biology and Medicine 26.5 (2013): 419-429.

Grimm, Robert, et al. "Self-gated MRI motion modeling for respiratory motion compensation in integrated PET/MRI." Medical image analysis 19.1 (2015): 110-120.

Deng, Zixin, et al. "Four-dimensional MRI using three-dimensional radial sampling with respiratory self-gating to characterize temporal phase-resolved respiratory motion in the abdomen." Magnetic resonance in medicine (2015).

Pang, Jianing, et al. "Accelerated whole-heart coronary MRA using motion-corrected sensitivity encoding with three-dimensional projection reconstruction." Magnetic resonance in medicine 73.1 (2015): 284-291.

Avants, Brian B., et al. "Symmetric diffeomorphic image registration with cross-correlation: evaluating automated labeling of elderly and neurodegenerative brain." Medical image analysis 12.1 (2008): 26-41.

Winkelmann, Stefanie, et al. "An optimal radial profile order based on the Golden Ratio for time-resolved MRI." IEEE transactions on medical imaging 26.1 (2007): 68-76.

Chan, Rachel W., et al. "Temporal stability of adaptive 3D radial MRI using multidimensional golden means." Magnetic resonance in medicine 61.2 (2009): 354-363.

* cited by examiner

RESPIRATORY PHASE-RESOLVED 3D BODY IMAGING USING ITERATIVE MOTION CORRECTION AND AVERAGE

CROSS-REFERENCE TO RELATED APPLICATIONS

This application claims the benefit of U.S. Provisional Application Ser. No. 62/334,108 filed May 10, 2016 which is incorporated herein by reference in its entirety.

TECHNOLOGY FIELD

The present invention relates generally to methods, systems, and apparatuses for improving respiratory phase-resolved 3D body imaging using iterative motion correction and averaging techniques. The disclosed techniques may be applied to enhance the characterization of motion and other portions of an acquired image to facilitate better diagnostic accuracy in clinical applications.

BACKGROUND

Magnetic Resonance Imaging (MRI) has been increasingly used for guiding therapy procedures, due to its distinct advantages when compared to competing imaging modalities. MRI provides excellent soft tissue contrast. Moreover, such procedures are free from ionizing radiations. Not only can the margins of target tumors be defined, it can also characterize respiratory induced organ motion from the same imaging session. Such information can be used for treatment simulation, adaption as well as repeated follow-up exams of the therapy procedure. Furthermore, it can also be helpful for the planning of minimally invasive surgery.

Real-time imaging is the most commonly used MR imaging method for such purpose, due to its broad availability, fast data acquisition and instantaneous image reconstruction on the fly. Typically, real-time images acquired with 2D or 3D acquisition were retrospectively sorted into different respiratory bins to resolve respiratory motion. The major drawbacks of such method, however, are limited spatial resolution (of 2D method) and poor temporal resolution (of 3D method) which hinder the accurate assessment of tumor motion information.

Recently, self-gated 4D (respiratory phase resolved 3D) techniques were developed to address limitations of conventional 4D MRI techniques. Using such self-gated methods, k-space data were continuously acquired under free breathing of patients. Self-gating data were analyzed for deriving respiratory motion information. Such self-gating data could be either periodically acquired using an additional self-gating line, or could be directly extracted from the actual imaging data itself.

FIG. 1 shows an example of 4D MRI sequence using koosh-ball k-space trajectory as an example. Based on motion information extracted from self-gating lines (projections in the superior-inferior direction), k-space data were sorted into different bins with each bin representing a unique respiratory motion status. Direct reconstruction of individual k-space bins results in 4D (respiratory phase resolved 3D) images.

FIG. 2 shows an example of 4D MR images acquired using the above described self-gating method. While soft tissues were clearly depicted, it is also evident that there is a substantial amount of background noise in the image, as well as streak artifact. This becomes increasingly prominent when a larger number of bins was selected in order to fully resolve the respiratory motion, since the number of k-space lines supporting the reconstruction of individual bin scales down with the number of respiratory bins.

SUMMARY

Embodiments of the present invention address and overcome one or more of the above shortcomings and drawbacks, by providing methods, systems, and apparatuses related to improving respiratory phase-resolved 3D body imaging using iterative motion correction and averaging techniques. This is achieved by first estimating the inter-bin respiratory motion followed by a motion corrected averaging process. Using this method, all acquired k-space lines were used to support the reconstruction of each individual bin, instead of using only a subset of k-space lines as in prior arts. This helps to improve the signal-to-noise ratio and reduce streaking artifacts of 4D MRI.

According to some embodiments, a method for performing 3D body imaging using iterative motion correction and averaging includes performing a free-breathing continuous 3D MRI acquisition of a patient to acquire k-space data over a plurality of breathing phases and dividing the k-space data into a plurality of k-space data bins. Each k-space data bin includes a portion of the k-space data corresponding to a distinct breathing phase. A plurality of 3D image sets are reconstructed from the plurality of k-space data bins. Each 3D image set corresponds to a distinct k-space data bin and may comprise magnitude images or complex images. A reference bin is selected from among the plurality of k-space data bins. For each bin other than the reference bin, a forward and inverse transform is calculated between the 3D image set corresponding to the bin and the 3D image set corresponding to the reference bin. Then, a motion corrected and averaged image is generated for each bin by (a) aligning the 3D image set from each other bin to the 3D image set corresponding to the bin using the forward and inverse transforms, and (b) averaging the aligned 3D image sets to yield the motion corrected and averaged image.

Various data acquisition schemes may be used with the aforementioned method. For example, in some embodiments, the free-breathing continuous 3D MRI acquisition is performed with a stack-of-stars trajectory or a stack-of-spirals trajectory. In these embodiments, the k-space data may be divided into a plurality of k-space data bins using self-gating signals extracted from k-space centers. In other embodiments, the free-breathing continuous 3D MRI acquisition is performed with a koosh-ball trajectory. In these embodiments, the k-space data may be divided into a plurality of k-space data bins using a self-gating line in the superior-inferior direction.

Various enhancements, refinements, and other modifications may be made to the methods discussed above. For example, in some embodiments, the reference bin corresponds to start of an expiration breathing phase. In other embodiments, each forward and inverse transform is performed using a symmetric diffeomorphic model.

According to one aspect of the present invention, as described in some embodiments, a method for performing 3D body imaging using iterative motion correction and averaging includes acquiring k-space data over a plurality of temporal phases and dividing the k-space data into a plurality of k-space data bins. Each k-space data bin includes a portion of the k-space data corresponding to a distinct temporal phase. A plurality of 3D image sets are reconstructed from the plurality of k-space data bins, each 3D image set corresponding to a distinct k-space data bin. A reference bin is selected from among the plurality of k-space data bins. Next, for each bin other than the reference bin, a forward and inverse transform is calculated between the 3D image set corresponding to the bin and the 3D image set corresponding to the reference bin. Then, a motion corrected and averaged image is generated for each bin by (a) aligning the 3D image set from each other bin to the 3D image set corresponding to the bin using the forward and inverse transforms, and (b) averaging the aligned 3D image sets to yield the motion corrected and averaged image.

According to other embodiments of the present invention, a system for performing 3D body imaging using iterative motion correction and averaging includes an imaging device comprising a plurality of coils, one or more processors, and a non-transitory, computer-readable storage medium in operable communication with the processors. The computer-readable storage medium contains one or more programming instructions that, when executed, cause the processors to perform one or more of the aforementioned methods (with or without the additional features described above).

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to improving respiratory phase-resolved 3D body imaging using iterative motion correction and averaging techniques. 4D respiratory phase-resolved 3D MRI has been increasingly used for the planning of radiotherapy and for guiding minimally invasive surgery. Recently developed self-gating methods showed great potential in 4D MRI by providing high imaging efficiency and isotropic spatial resolution. However, images of individual phases may suffer from decreased SNR and increased streaking artifact since only a subset of data were used for reconstruction. A motion correction and average ("MoCoAve") framework is described herein that addresses such limitations. The techniques described herein provide a significant improvement to the SNR and image quality without compromising motion information of the target tumor.

Figure 1:
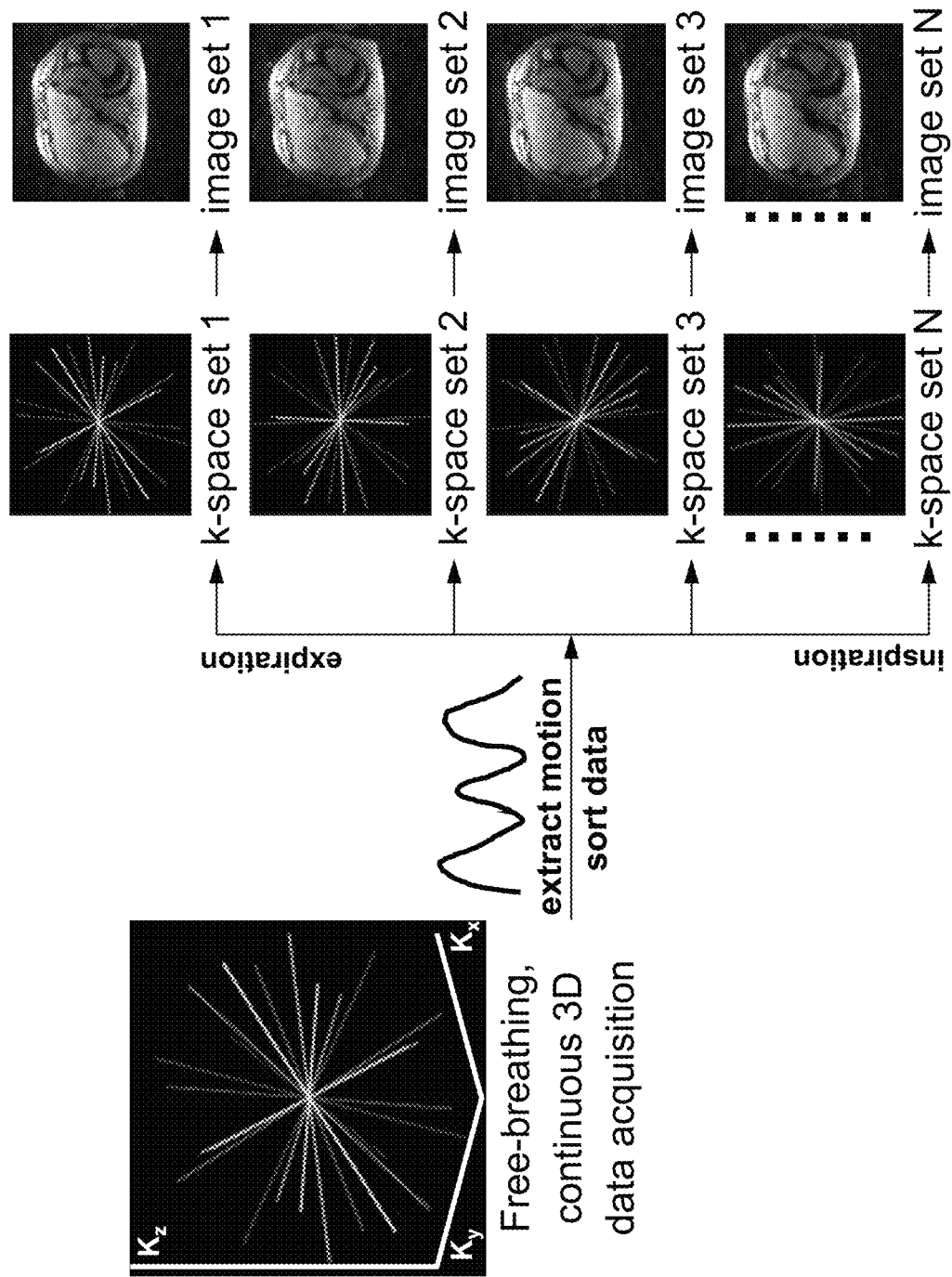
FIG. 1 shows schematic workflow of a 4D MRI sequence using 3D radial koosh-ball k-space trajectory.
Figure 2:
FIG. 2 illustrates an example 4D MR images from one selected respiratory phase (end expiratory in this case)
Figure 2:
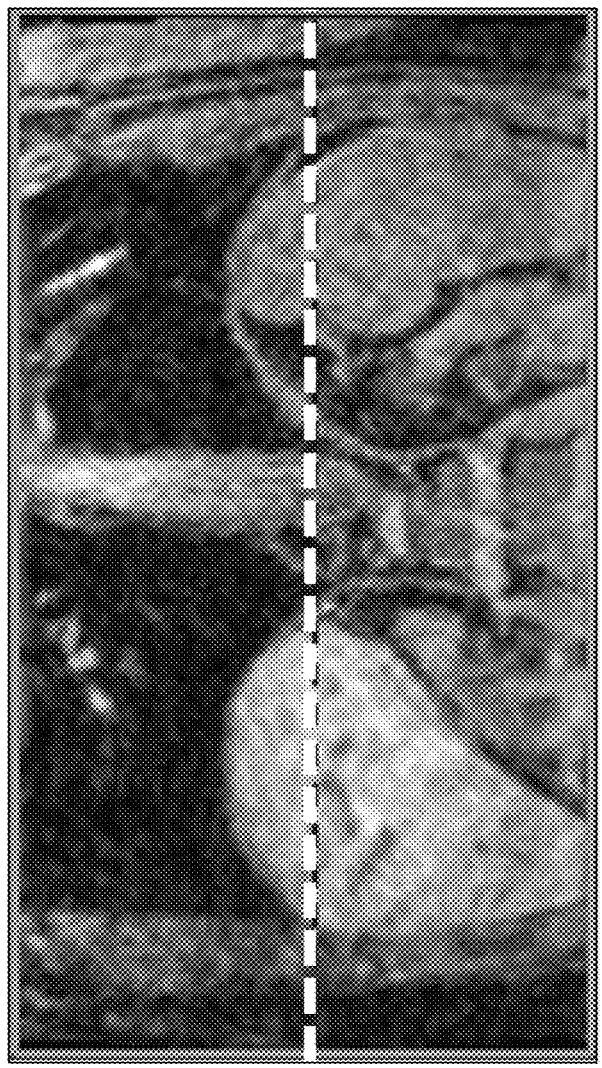
Figure 3:
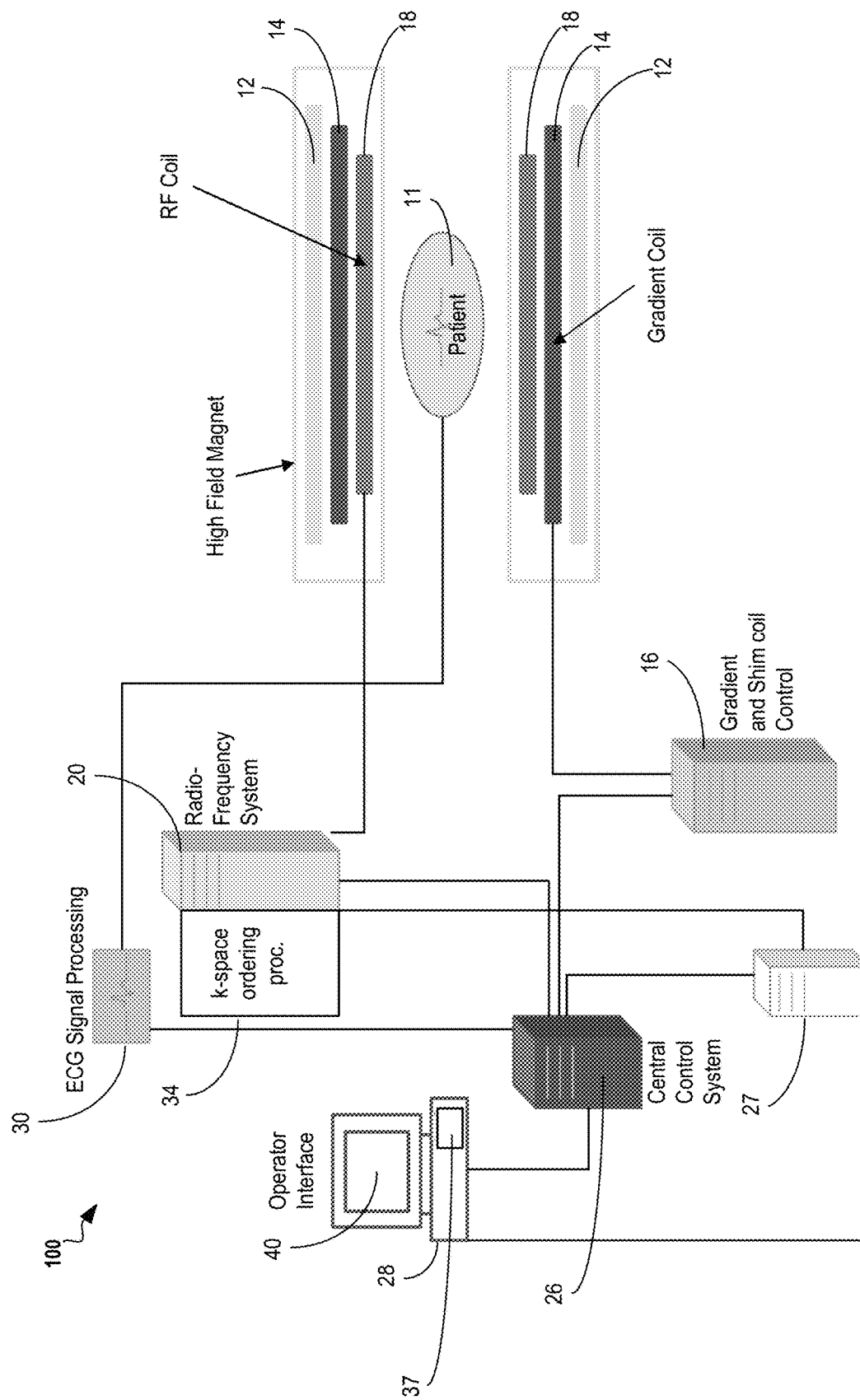
FIG. 3 shows a system for ordering acquisition of frequency domain components representing magnetic resonance image data for storage in a k-space storage array, as used by some embodiments of the present invention.

FIG. 3 shows an example MRI system 100 where the MoCoAve framework discussed herein may be implemented, according to some embodiments. This system 100 orders the acquisition of frequency domain components representing MRI data for storage in a k-space storage array. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by 90 degrees or by 180 degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 3, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which the radius of respective corresponding individual data elements increases and decreases along a substantially spiral path as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components which is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 3, display processor 37 processes the magnetic resonance signals to reconstruct one or more images for presentation on display 40, for example. Various techniques may be used for reconstruction. For example, in conventional systems, an optimization algorithm is applied to iteratively solve a cost function which results in the reconstructed image.

Figure 4A:
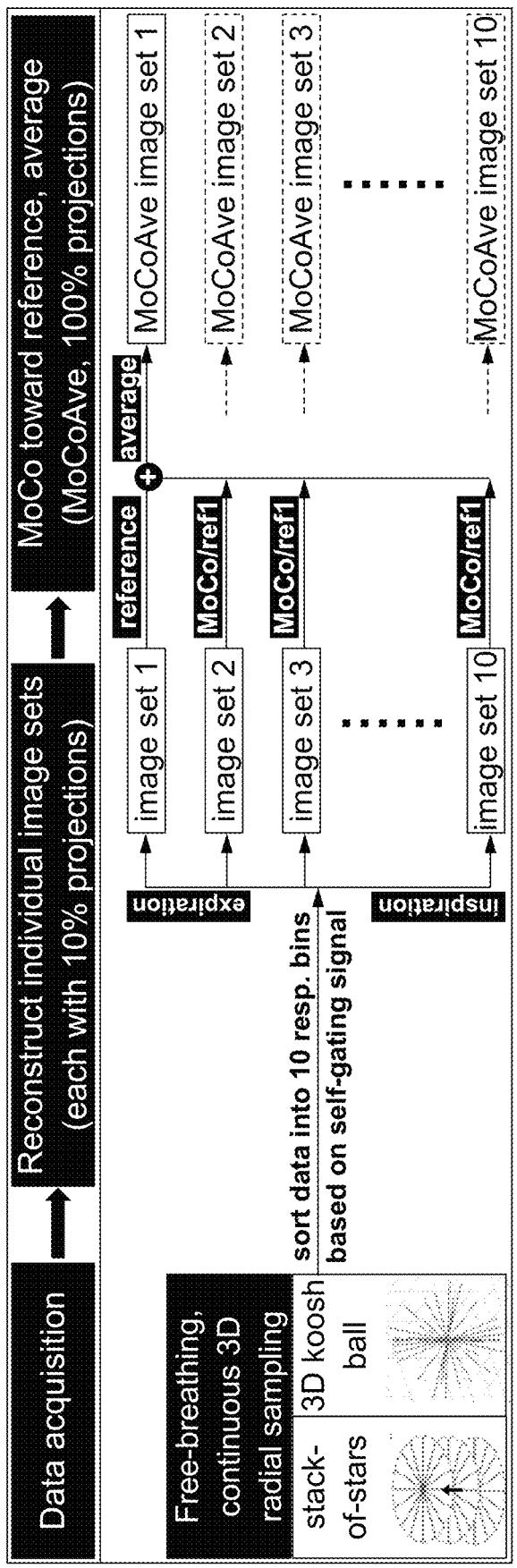
FIG. 4A provides an schematic of an example MoCoAve method, according to some of the embodiments of the present invention.

FIG. 4A illustrates the schematic flowchart of a 4D MRI method that may be used with the system 100 illustrated in FIG. 3 to improve respiratory phase-resolved 3D body imaging using iterative motion correction and averaging techniques. Using a 4D MRI method, a 3D image set was reconstructed from each bin using the corresponding subset of k-space data. The MoCoAve process was subsequently performed on all under-sampled respiratory phase image series. In this example, image set 1 is selected to be the reference bin. Forward and inverse transform between image sets 2-9 and image 1 could be computed. Then, the MoCoAve image of each phase is produced by first aligning all phases to this phase using the respective combinations of transforms, and then averaging the warped images to enhance the image quality.

Figure 4B:
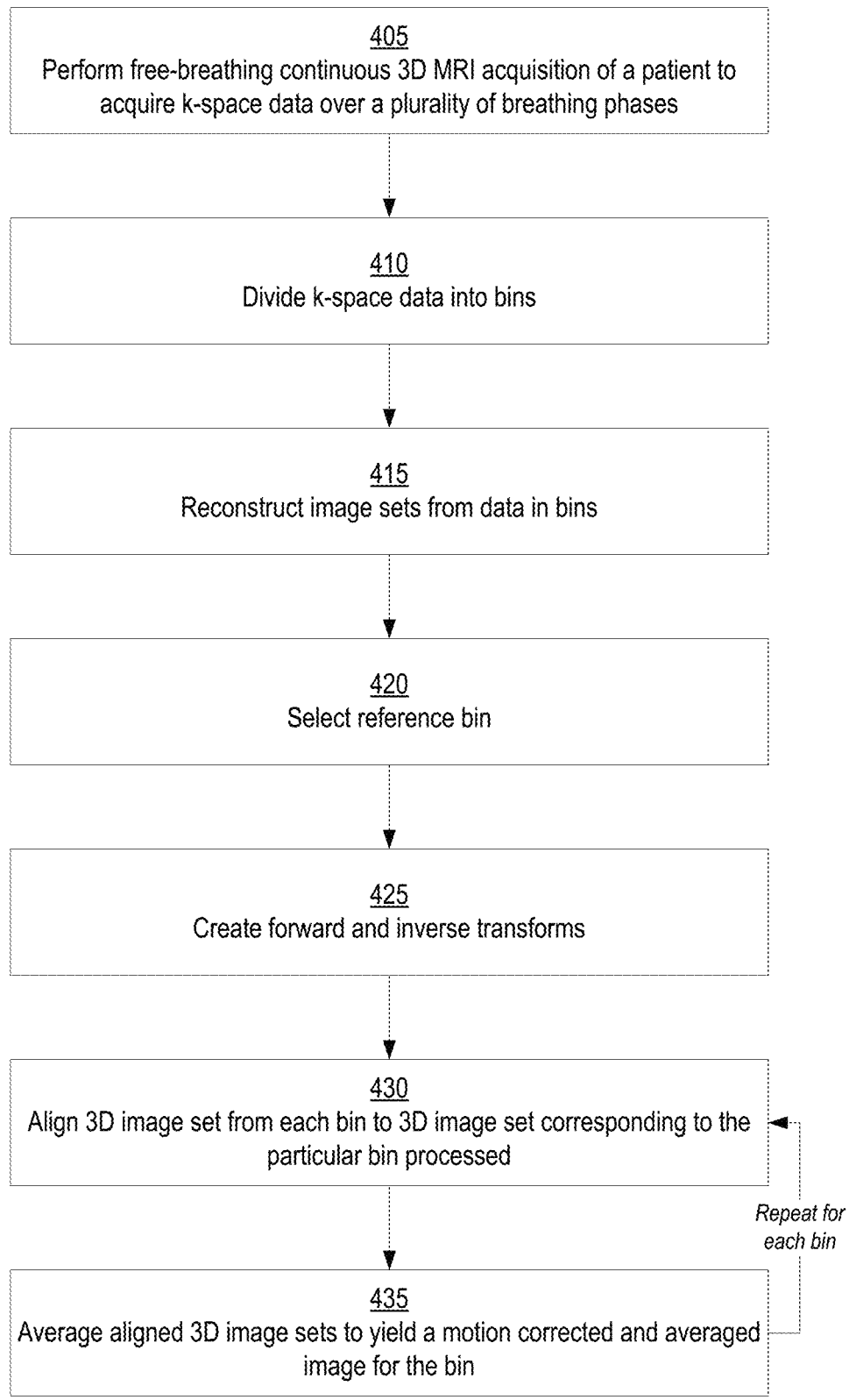
FIG. 4B provides a flowchart which further illustrates the details of the method shown in FIG. 4A.

FIG. 4B provides a flowchart which further illustrates the details of the method shown in FIG. 4A, as it may be implemented in some embodiments. Starting at step 405, a free-breathing continuous 3D MRI acquisition of a patient is performed to acquire k-space data over a plurality of breathing phases. Next, at step 410, the k-space data acquired at step 405 is divided into k-space data bins. Each k-space data bin includes a portion of the k-space data corresponding to a distinct breathing phase. The number of bins can vary depending, for example, on the clinical application. For example, in embodiments, where the goal is to observe a smooth motion pattern over the breathing cycle, a large number of bins may be used. Conversely, if the goal is only to observe morphology information, then a smaller number of bins may be used. In some embodiments, the number of bins is explicitly specified by the MRI system operator. In other embodiments, the number of bins may be automatically specified based on factors such as the type of scan being performed or the relative noise present in the acquired data.

Various trajectories generally known in the art may be adapted for performing the data acquisition at step 405 and the division of data may be adjusted accordingly based on the characteristics of the trajectory. For example, in some embodiments, the acquisition is performed with a stack-of-stars trajectory and the k-space data is divided using self-gating signals extracted from k-space centers. In other embodiments, the acquisition is performed with a koosh-ball trajectory and the k-space data is divided using a self-gating line in the superior-inferior direction.

Although the acquisition is described above with reference to respiratory phase, it is not limited as such. More generically, the techniques described herein are applicable to any type of temporal phases that may occur during the image. For example, in other embodiments of the present invention, the general method shown in FIG. 4A and FIG. 4B may be adapted to applications where the temporal phases correspond to the patient's cardiac cycle.

Continuing with reference to FIG. 4B, at step 415, 3D image sets are reconstructed from the k-space data bins. Each reconstructed 3D image set corresponds to a distinct k-space data bin and comprises one or more images. These images may be magnitude images or complex images. For some implementations, it may be more attractive to utilize complex images because complex MR images show Gaussian noise distribution with zero mean while magnitude images show Rician noise distribution with non-zero mean, averaging complex images yields higher SNR ratios than directly averaging magnitude images.

Next at step 420, a reference bin is selected from among the k-space data bins. In general, any of the bins may be selected as the reference bin. For example, in one embodiment, the reference bin corresponds to start of an expiration breathing phase. At step 425, both forward and inverse transforms are calculated between the 3D image set corresponding to the bin and the 3D image set corresponding to the reference bin. In some embodiments, the transform is performed using two arbitrary bins included in the plurality of k-space data bins. Each forward and inverse transforms may be calculated, for example, using a symmetric diffeomorphic model, as described in Avants BB, Epstein CL, Grossman M, Gee JC. *Symmetric diffeomorphic image registration with cross-correlation: evaluating automated labeling of elderly and neurodegenerative brain*. Med Image Anal. 2008 12:26-41. Aside from the symmetric diffeomorphic model, other techniques generally known in the art may be used for calculating the transforms in other embodiments of the present invention.

At steps 430 and 435 a motion corrected and averaged image is generated for each bin. First, at step 430 the 3D image set from each bin is aligned to the 3D image set corresponding to the particular bin being processed using the transforms determined at step 425. Then, at step 435, the aligned 3D image sets are averaged to yield the motion corrected and averaged image (i.e., a MoCoAve image) for the bin.

Figure 5:
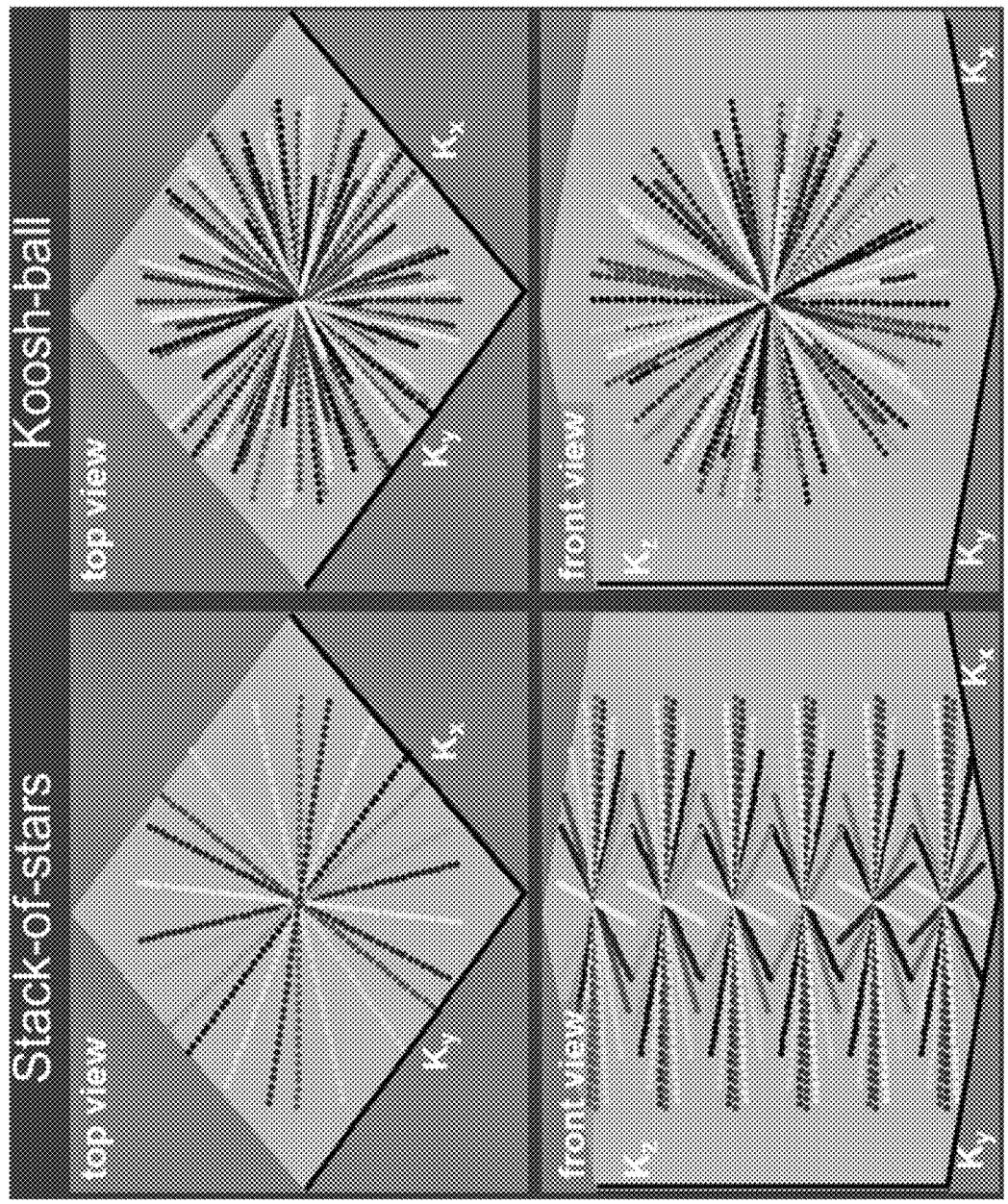
FIG. 5 provides an example k-space ordering of two prototype 4D MRI sequences using stack-of-stars and koosh-ball sampling trajectories that may be used in some embodiments.
Figure 6:
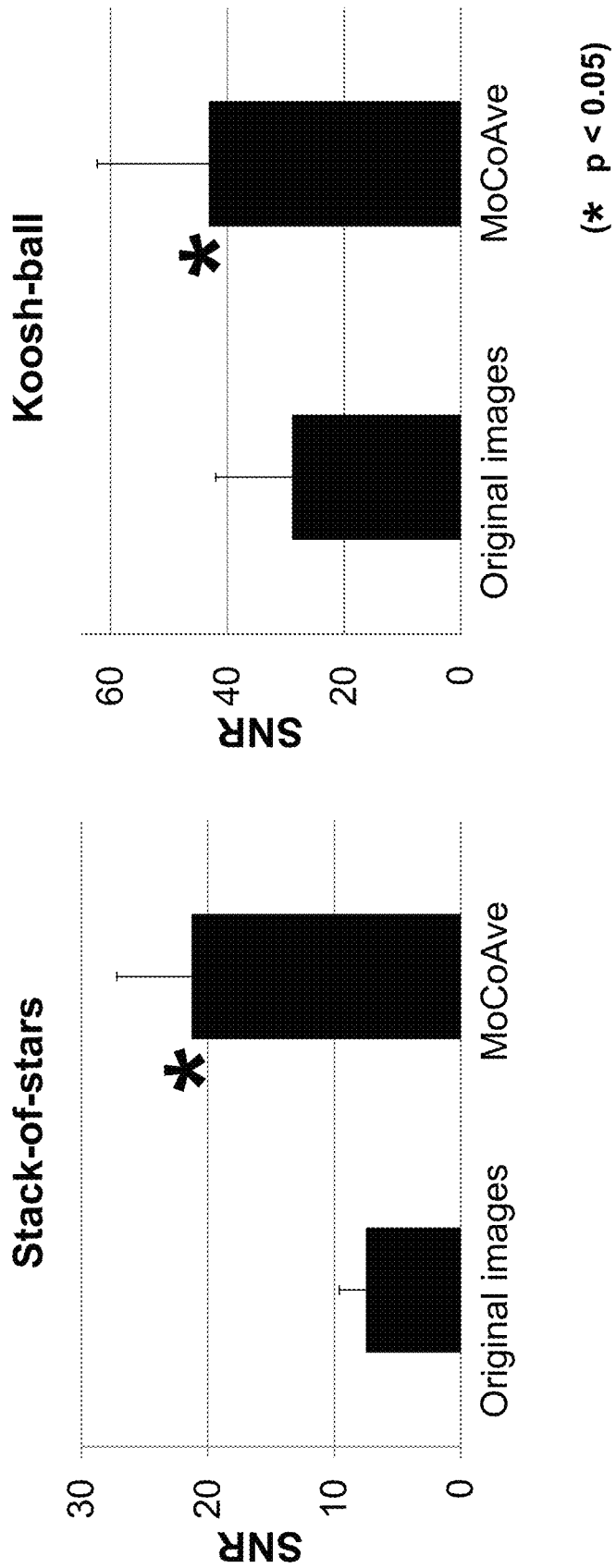
FIG. 6 provides an example of quantitative results of signal-to-noise ratio (SNR) measurement without and with MoCoAve, as it may be implemented in some embodiments.

To validate the MoCoAve techniques described herein, two prototype 4D MRI sequences were implemented on 3T clinical scanners (MAGNETOM Verio, Biograph mMR, Siemens Healthcare). FIG. 5 illustrates the k-space trajectory of these two sequences, using stack-of-stars and koosh-ball k-space ordering, respectively. In both cases, golden angle trajectory was used to ensure uniform k-space distribution.

A pilot study of five patients with a confirmed tumor (3 pancreatic, 1 liver, 1 lung) were scanned on a 3T clinical scanner. Seven 4D MR scans (4 koosh-ball, 3 stack-of-stars) were acquired using 10-degree Fast Low Angle Shot (FLASH) readout with parameters listed in the table below.

|  | Stack-of-Stars | Koosh-ball |
| --- | --- | --- |
| Partitions | 104 | 256 |
| Radial projections | 1504 (per partition) | 73005 |
| Field of View ($mm^3$, X-Y-Z) | 380 × 380 × 206 | 300 × 300 × 300 |
| Voxel size ($mm^3$) | 1.98 × 1.98 × 1.98 | 1.56 × 1.56 × 1.56 |
| Repetition Time/Echo | 3.4/1.7 | 5.8/2.6 |
| Self-gated signal interval (ms) | 353 | 98 |
| Time to Acquisition (min) | 9.5 | 6.5 |

SNR and motion trajectory of tumors were assessed from each respiratory phase using images directly reconstructed from individual bins, as well as corresponding images after MoCoAve. SNR was defined as signal intensity in the liver divided by the standard deviation of background air signal. For each patient, ROIs for signal measurement were matched between different image sets. In total 70 pairs of volumetric images were acquired. Quantitative analysis showed significantly improved SNR using the proposed MoCoAve method (mean±SD without and with MoCoAve: stack-of-stars: 7.5±2.1 vs 21.3±5.9, $p<0.01$ koosh-ball: 28.9±13.1 vs 43.2±19.1, $p<0.01$).

For motion assessment, tumor volumes were drawn on the end expiration phase of 4D MR images. Such contour was then mapped to the other respiratory phases using a B-spline based deformable registration in VelocityAI (Varian, Palo Alto, Calif.). The coordinates of each contour's center of mass was then extracted for tumor motion trajectory evaluation.

Figure 7:
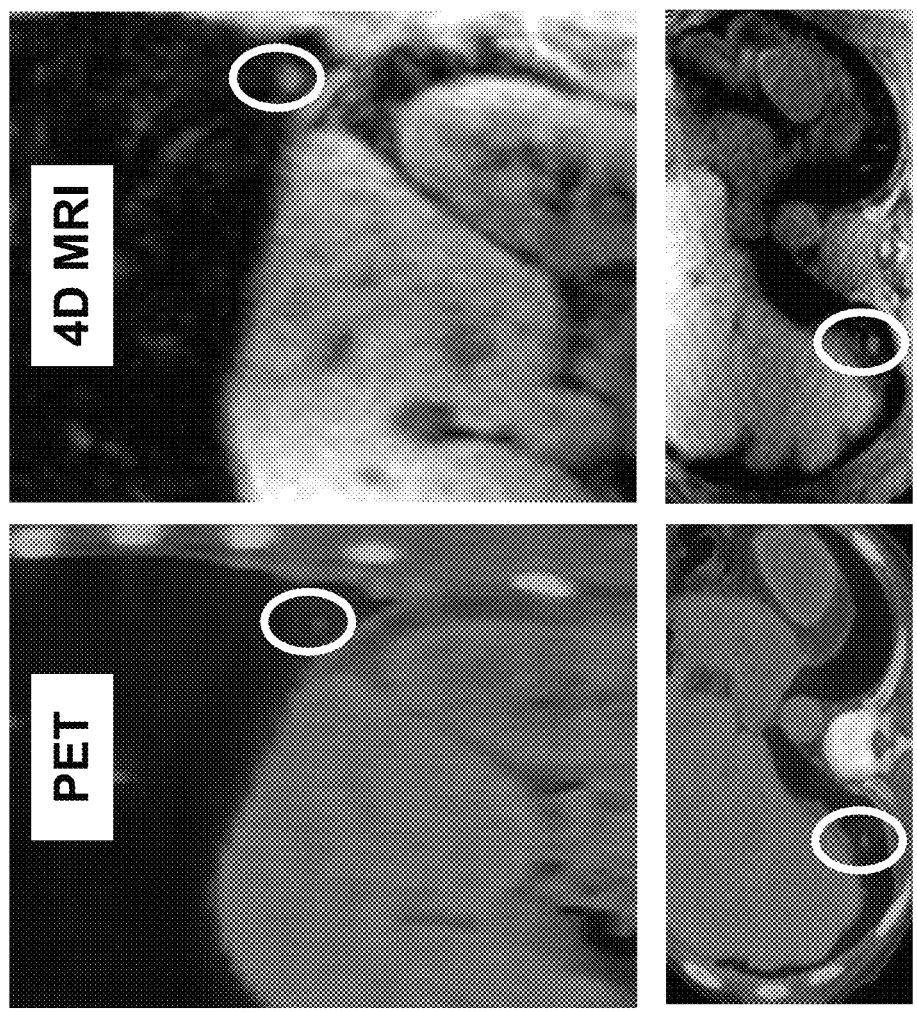
FIG. 7 shows an example lung nodule of a patient identified from both 4D MRI and positron emission tomography (PET) images.
Figure 8:
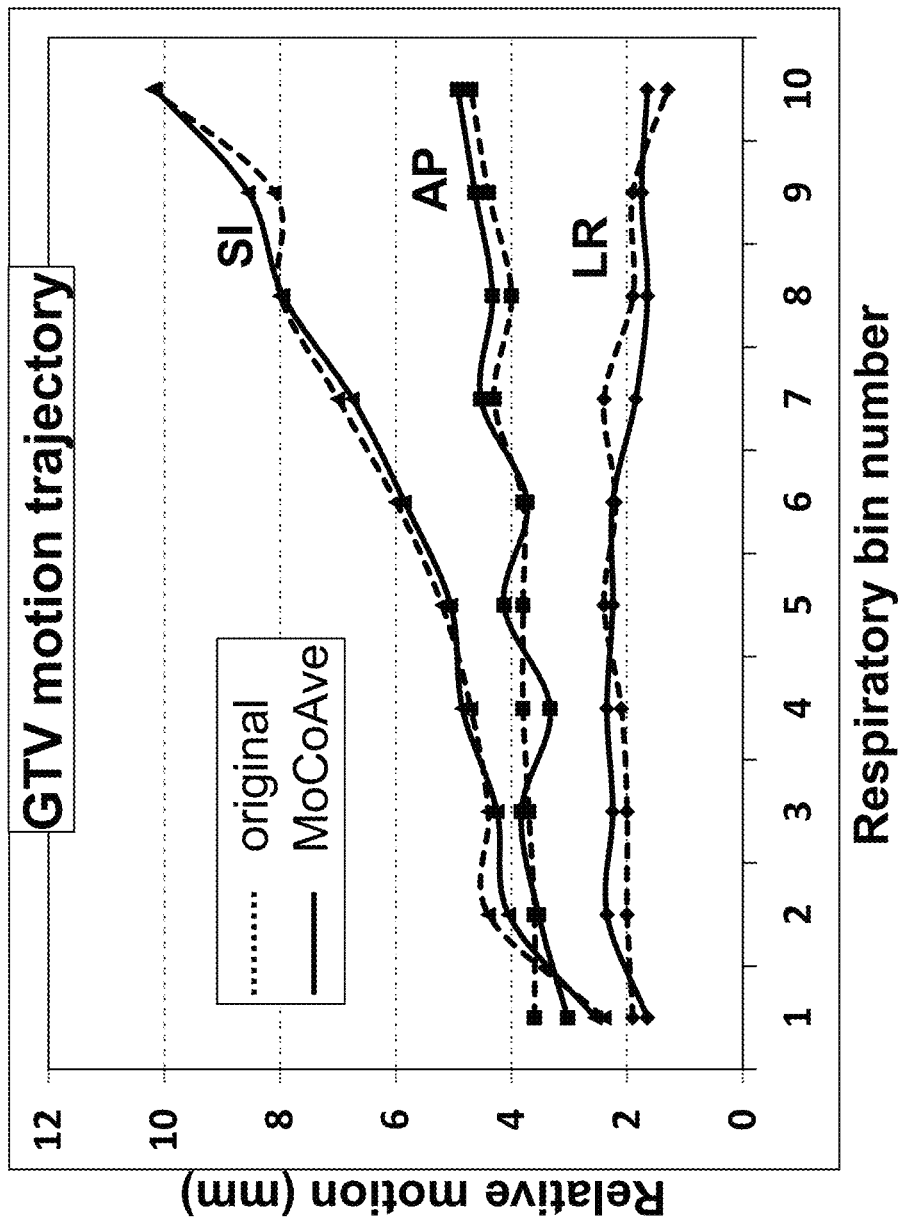
FIG. 8 presents motion trajectory data of the nodule shown in FIG. 7 at different respiratory phases.

FIG. 7 shows a lung cancer nodule of a patient visualized in MR and PET images. FIG. 8 presents motion trajectory data of the nodule at different respiratory phases. As shown in the figures, there is excellent agreement on motion between two 4D image sets, without and with the MoCoAve processing. This indicates that motion information is well preserved and no negative impact on motion information was introduced by the MoCoAve process. Results from five patients showed excellent correlation of motion trajectory measured from images without and with MoCoAve. Correlation coefficients were 0.94±0.10, 0.88±0.12, and 0.74±0.16, respectively, in the superior-inferior, anterior-posterior and left-right directions. Note such respiratory motion was dominant in the superior-inferior direction where highest correlation was observed from the measurement.

Figure 9:
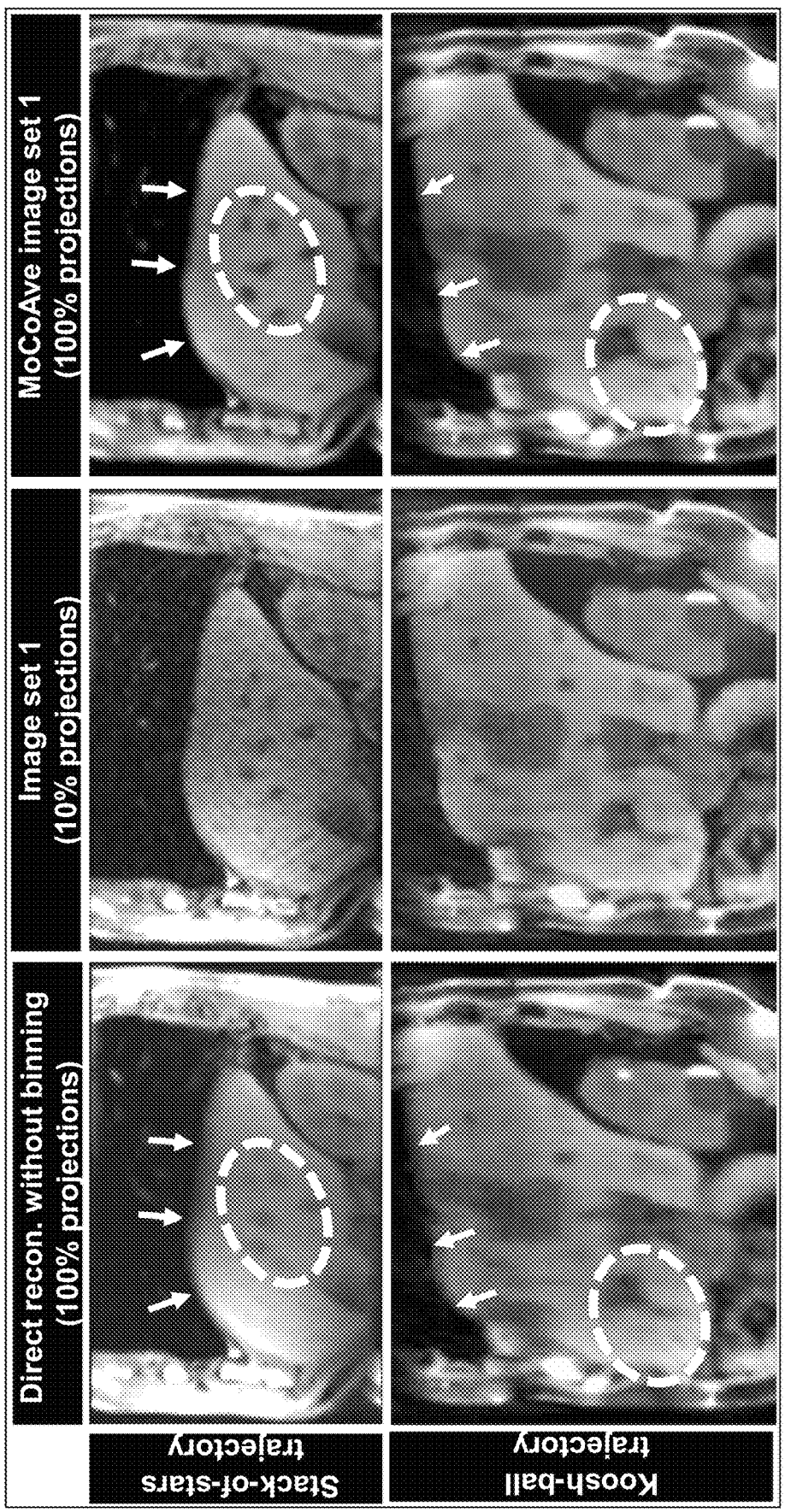
FIG. 9 shows representative images acquired from two patients using stack-of-stars and koosh-ball k-space trajectory.

FIG. 9 shows representative images acquired from two patients using stack-of-stars (top row) and a koosh-ball (bottom row) k-space trajectory. Without binning k-space data using self-gating signal, images were quite blurry (left column) for both stack-of-stars and koosh-ball images. Visual signal-to-noise ratio was high with all k-space data used for reconstructing these images. By sorting k-space data into 10 respiratory bins, reconstructed images (middle column) were very sharp with lung-liver interface and structures well depicted. SNR was low since only a portion (10% in this case) of k-space data was used to support each respiratory bin. By using the MoCoAve method (right column), not only the image sharpness was preserved, high SNR and good quality images were achieved.

Figure 10:
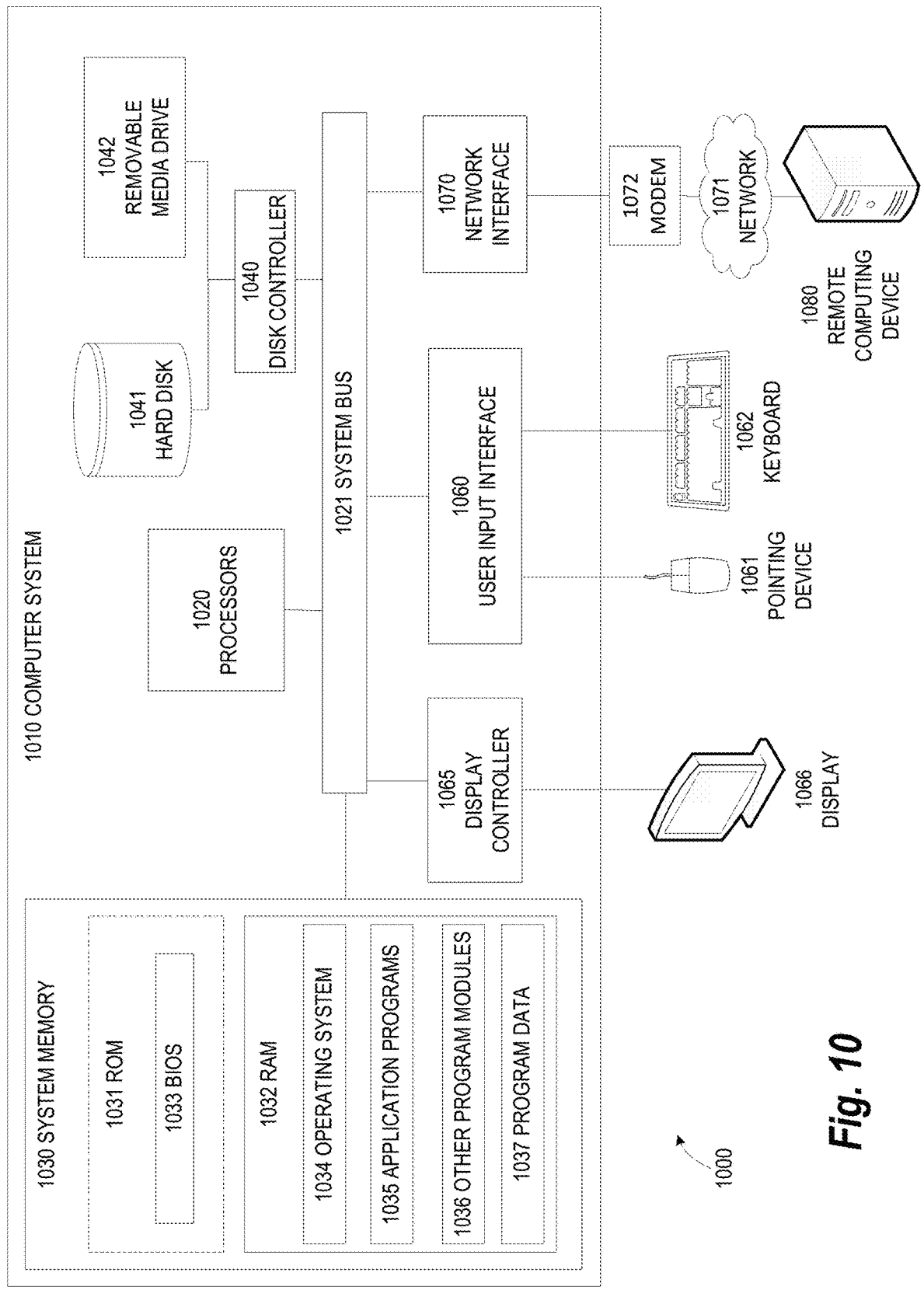
FIG. 10 illustrates an exemplary computing environment within which embodiments of the invention may be implemented.

FIG. 10 illustrates an exemplary computing environment 1000 within which embodiments of the invention may be implemented. For example, in some embodiments, the computing environment 1000 may be used to implement one or more of the components illustrated in the system 100 of FIG. 3. The computing environment 1000 may include computer system 1010, which is one example of a computing system upon which embodiments of the invention may be implemented. Computers and computing environments, such as computer system 1010 and computing environment 1000, are known to those of skill in the art and thus are described briefly here.

As shown in FIG. 10, the computer system 1010 may include a communication mechanism such as a bus 1021 or other communication mechanism for communicating information within the computer system 1010. The computer system 1010 further includes one or more processors 1020 coupled with the bus 1021 for processing the information. The processors 1020 may include one or more central processing units (CPUs), graphical processing units (GPUs), or any other processor known in the art.

The computer system 1010 also includes a system memory 1030 coupled to the bus 1021 for storing information and instructions to be executed by processors 1020. The system memory 1030 may include computer readable storage media in the form of volatile and/or nonvolatile memory, such as read only memory (ROM) 1031 and/or random access memory (RAM) 1032. The system memory RAM 1032 may include other dynamic storage device(s) (e.g., dynamic RAM, static RAM, and synchronous DRAM). The system memory ROM 1031 may include other static storage device(s) (e.g., programmable ROM, erasable PROM, and electrically erasable PROM). In addition, the system memory 1030 may be used for storing temporary variables or other intermediate information during the execution of instructions by the processors 1020. A basic input/output system (BIOS) 1033 containing the basic routines that help to transfer information between elements within computer system 1010, such as during start-up, may be stored in ROM 1031. RAM 1032 may contain data and/or program modules that are immediately accessible to and/or presently being operated on by the processors 1020. System memory 1030 may additionally include, for example, operating system 1034, application programs 1035, other program modules 1036 and program data 1037.

The computer system 1010 also includes a disk controller 1040 coupled to the bus 1021 to control one or more storage devices for storing information and instructions, such as a hard disk 1041 and a removable media drive 1042 (e.g., floppy disk drive, compact disc drive, tape drive, and/or solid state drive). The storage devices may be added to the computer system 1010 using an appropriate device interface (e.g., a small computer system interface (SCSI), integrated device electronics (IDE), Universal Serial Bus (USB), or FireWire).

The computer system 1010 may also include a display controller 1065 coupled to the bus 1021 to control a display 1066, such as a cathode ray tube (CRT) or liquid crystal display (LCD), for displaying information to a computer user. The computer system includes an input interface 1060 and one or more input devices, such as a keyboard 1062 and a pointing device 1061, for interacting with a computer user and providing information to the processor 1020. The pointing device 1061, for example, may be a mouse, a trackball, or a pointing stick for communicating direction information and command selections to the processor 1020 and for controlling cursor movement on the display 1066. The display 1066 may provide a touch screen interface which allows input to supplement or replace the communication of direction information and command selections by the pointing device 1061.

The computer system 1010 may perform a portion or all of the processing steps of embodiments of the invention in response to the processors 1020 executing one or more sequences of one or more instructions contained in a memory, such as the system memory 1030. Such instructions may be read into the system memory 1030 from another computer readable medium, such as a hard disk 1041 or a removable media drive 1042. The hard disk 1041 may contain one or more datastores and data files used by embodiments of the present invention. Datastore contents and data files may be encrypted to improve security. The processors 1020 may also be employed in a multi-processing arrangement to execute the one or more sequences of instructions contained in system memory 1030. In alternative embodiments, hard-wired circuitry may be used in place of or in combination with software instructions. Thus, embodiments are not limited to any specific combination of hardware circuitry and software.

As stated above, the computer system 1010 may include at least one computer readable medium or memory for holding instructions programmed according to embodiments of the invention and for containing data structures, tables, records, or other data described herein. The term "computer readable medium" as used herein refers to any medium that participates in providing instructions to the processor 1020 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1041 or removable media drive 1042. Non-limiting examples of volatile media include dynamic memory, such as system memory 1030. Non-limiting examples of transmission media include coaxial cables, copper wire, and fiber optics, including the wires that make up the bus 1021. Transmission media may also take the form of acoustic or light waves, such as those generated during radio wave and infrared data communications.

The computing environment 1000 may further include the computer system 1010 operating in a networked environment using logical connections to one or more remote computers, such as remote computer 1080. Remote computer 1080 may be a personal computer (laptop or desktop), a mobile device, a server, a router, a network PC, a peer device or other common network node, and typically includes many or all of the elements described above relative to computer system 1010. When used in a networking environment, computer system 1010 may include modem 1072 for establishing communications over a network 1071, such as the Internet. Modem 1072 may be connected to bus 1021 via user network interface 1070, or via another appropriate mechanism.

Network 1071 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1010 and other computers (e.g., remote computer 1080). The network 1071 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1071.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for performing 3D body imaging using iterative motion correction and averaging, the method comprising:
    performing a free-breathing continuous 3D MRI acquisition of a patient to acquire k-space data over a plurality of breathing phases;
    dividing the k-space data into a plurality of k-space data bins, wherein each k-space data bin includes a portion of the k-space data corresponding to a distinct breathing phase;
    reconstructing a plurality of 3D image sets from the plurality of k-space data bins, each 3D image set corresponding to a distinct k-space data bin;
    selecting a reference bin from among the plurality of k-space data bins;
    for each bin other than the reference bin, calculating a forward and inverse transform between the 3D image set corresponding to the bin and the 3D image set corresponding to the reference bin; and
    generating a motion corrected and averaged image for each bin by (a) aligning the 3D image set from each other bin to the 3D image set corresponding to the bin using the forward and inverse transforms, and (b) averaging the aligned 3D image sets to yield the motion corrected and averaged image.

2. The method of claim 1, wherein the free-breathing continuous 3D MRI acquisition is performed with a stack-of-stars trajectory or a stack-of-spirals trajectory.

3. The method of claim 2, wherein the k-space data is divided into a plurality of k-space data bins using self-gating signals extracted from k-space centers.

4. The method of claim 1, wherein the free-breathing continuous 3D MRI acquisition is performed with a koosh-ball trajectory.

5. The method of claim 4, wherein the k-space data is divided into a plurality of k-space data bins using a self-gating line in the superior-inferior direction.

6. The method of claim 1, wherein the reference bin corresponds to the start of an expiration breathing phase.

7. The method of claim 1, wherein each forward and inverse transform is performed using a symmetric diffeomorphic model.

8. The method of claim 1, wherein the plurality of 3D image sets comprise magnitude images.

9. The method of claim 1, wherein the plurality of 3D image sets comprise complex images.

10. A method for performing 3D body imaging using iterative motion correction and averaging, the method comprising:
    acquiring k-space data over a plurality of temporal phases;
    dividing the k-space data into a plurality of k-space data bins, wherein each k-space data bin includes a portion of the k-space data corresponding to a distinct temporal phase;
    reconstructing a plurality of 3D image sets from the plurality of k-space data bins, each 3D image set corresponding to a distinct k-space data bin;
    selecting a reference bin from among the plurality of k-space data bins;
    for each bin other than the reference bin, calculating forward and inverse transforms between the 3D image set corresponding to the bin and the 3D image set corresponding to the reference bin; and
    generating a motion corrected and averaged image for each bin by (a) aligning the 3D image set from each other bin to the 3D image set corresponding to the bin using the forward and inverse transforms, and (b) averaging the aligned 3D image sets to yield the motion corrected and averaged image.

11. The method of claim 10, wherein the k-space data is acquired using a stack-of-stars trajectory or a stack-of-spirals trajectory.

12. The method of claim 11, wherein the k-space data is divided into a plurality of k-space data bins using self-gating signals extracted from k-space centers.

13. The method of claim 10, wherein the k-space data is acquired using a koosh-ball trajectory.

14. The method of claim 13, wherein the k-space data is divided into a plurality of k-space data bins using a self-gating line in the superior-inferior direction.

15. The method of claim 10, wherein the reference bin corresponds to the start of an expiration breathing phase.

16. The method of claim 10, wherein each forward and inverse transform is performed using a symmetric diffeomorphic model.

17. The method of claim 10, wherein the plurality of 3D image sets comprise magnitude images.

18. The method of claim 10, wherein the plurality of 3D image sets comprise complex images.

19. A system for performing 3D body imaging using iterative motion correction and averaging, the system comprising:
    an imaging device comprising a plurality of coils;
    one or more processors; and
    a non-transitory, computer-readable storage medium in operable communication with the processor, wherein the computer-readable storage medium contains one or more programming instructions that, when executed, cause the processors to:
    use the plurality of coils to acquire k-space data over a plurality of breathing phases;
    divide the k-space data into a plurality of k-space data bins, wherein each k-space data bin includes a portion of the k-space data corresponding to a distinct breathing phase;

reconstruct a plurality of 3D image sets from the plurality of k-space data bins, each 3D image set corresponding to a distinct k-space data bin;
select a reference bin from among the plurality of k-space data bins;
for each bin other than the reference bin, calculate a forward and inverse transform between the 3D image set corresponding to the bin and the 3D image set corresponding to the reference bin; and
generate a motion corrected and averaged image for each bin by (a) aligning the 3D image set from each other bin to the 3D image set corresponding to the bin using the forward and inverse transforms, and (b) averaging the aligned 3D image sets to yield the motion corrected and averaged image.

* * * * *